US00PP32290P2

(12) United States Plant Patent
Hansen

(10) Patent No.: US PP32,290 P2
(45) Date of Patent: Oct. 6, 2020

(54) ***CAMPANULA* PLANT NAMED 'CHURCH BELLS'**

(50) Latin Name: ***Campanula glomerata* L.**
Varietal Denomination: Church Bells

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/873,092

(22) Filed: Jan. 30, 2020

(51) Int. Cl.
*A01H 5/02* (2018.01)
*A01H 6/26* (2018.01)

(52) U.S. Cl.
USPC ..... Plt./414

(58) Field of Classification Search
USPC ..... Plt./263.1, 414
See application file for complete search history.

*Primary Examiner* — Susan McCormick Ewoldt
*Assistant Examiner* — Karen M Redden

(57) ABSTRACT

The new and distinct Bellflower plant, *Campanula* plant named 'Church Bells' with dense, compact, mounded, upright habit; dark-green lanceolate foliage and numerous violet-purple campanulate flowers over a seven week period clustered at nodes and ends of on upright stems beginning in late June.

1 Drawing Sheet

Botanical designation: *Campanula glomerata* L.
Cultivar denomination: 'Church Bells'.

STATEMENT REGARDING PRIOR DISCLOSURES UNDER 37 CFR 1.77(b)(6)

The non-enabling disclosure of the claimed plant was made by Walters Gardens, Inc. on Feb. 1, 2019 when the claimed plant was displayed as a photograph with a brief description in a website maintained by Walters Gardens, Inc. Subsequently, the new plant was advertised in the "Walters Gardens 19-20 Catalog" first distributed on May 29, 2019 and the initial sales was on Jul. 8, 2019. Walters Gardens, Inc. obtained the new plant and all information about the new plant from the inventor. No plants of *Campanula* 'Church Bells' have been sold, in this country or anywhere in the world as of the filing date of this application, nor has any disclosure of the new plant been made, more than one year prior the filing date of this application, and such disclosure within one year was either derived directly or indirectly from the inventor.

BACKGROUND OF THE PLANT

The present invention relates to the new and distinct clustered bellflower herein also referred to as *Campanula* 'Church Bells', by the cultivar name, 'Church Bells', or as the new plant. The new plant was derived from seed collected on Oct. 8, 2014 from a plant in an isolation block, in a research facility in Zeeland, Mich., that was an unreleased, proprietary, selection identified by the breeder code "Lavender". The specific male parent was a sibling of "Lavender". The single seedling represented by 'Church Bells' was selected from a group of seedlings by the inventor, isolated and compared in subsequent years to other *Campanula* and subsequently found to be different from all cultivars known to the discoverer and eventually given the breeder code 14-1-4.

Asexual propagation at the same nursery in Zeeland, Mich., USA by basal cuttings has shown 'Church Bells' to be stable and reproduce true to type in successive generations since late June 2016.

SUMMARY OF THE PLANT

*Campanula* 'Church Bells' has not been observed in all possible environmental conditions. The phenotype may vary slightly with changes in environments such as light intensity, fertility, water availability, etc. without, however any variation in genotype.

*Campanula* 'Church Bells' is distinct from all cultivars known to the inventor in the following traits:

1. Narrow serrate foliage with compact height and dense mounded habit.
2. Heavily-branched with violet-purple bell-shaped flowers clustered at the nodes and ends of upright stems.
3. Dark green foliage.
4. Long flowering period beginning with concentration in late-June and continuing for about 7 weeks.

Plants of *Campanula* 'Church Bells' are most similar to 'Allgentibl' U.S. Plant Pat. No. 24,687. 'Freya' U.S. Plant Pat. No. 22,738, 'Emerald' U.S. Plant Pat. No. 18,343, 'Allgentitwist' U.S. Plant Pat. No. 25,403, 'Chico Rosa' U.S. Plant Pat. No. 26,834 and 'Chico Merano' U.S. Plant Pat. No. 26,867. 'Allgentibl' is shorter in habit and produces fewer flowers over a shorter period of time. 'Freya' has a much larger less compact habit in both height and width. 'Emerald' is similar in habit, but the flower color is a light purple and the new plants is more prolific in flowering. 'Allgentitwist' has slightly taller habit with white sepals. 'Chico Rosa' has a slightly taller and much broader habit with light purple flowers. 'Chico Merano' has a broader habit and a slightly different hue of purple flowers. "Lavender" has lavender purple flowers.

BRIEF DESCRIPTION OF THE DRAWINGS

The color drawings illustrate the overall characteristics of *Campanula* 'Church Bells' as a four-year-old plant. The colors are as true as reasonably possible given the technology available. The color values may vary slightly depending on light intensity and quality.

DETAILED BOTANICAL DESCRIPTION

Figure 1:
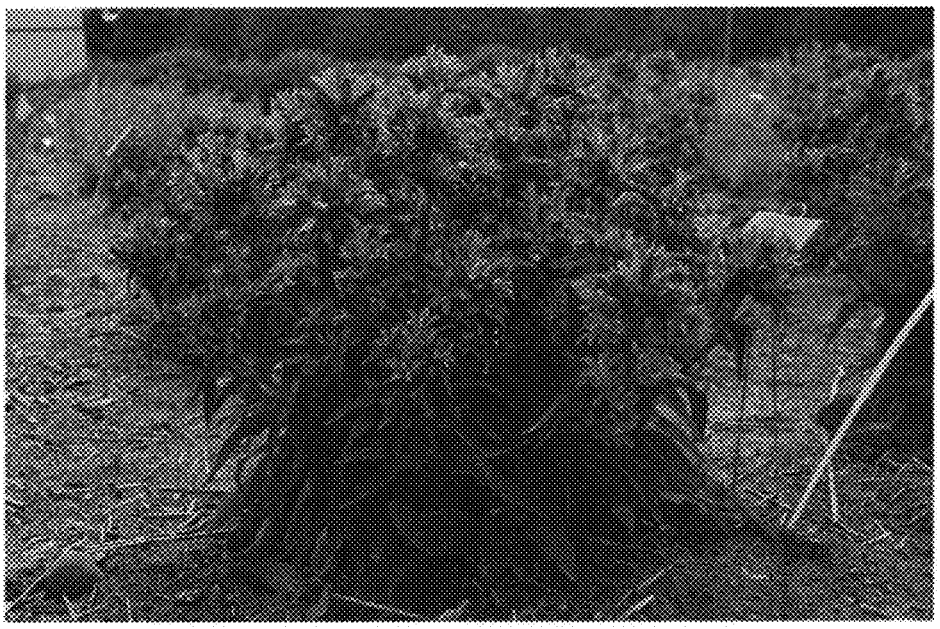
FIG. 1 shows the new plant in a landscape environment in peak flower.
Figure 2:
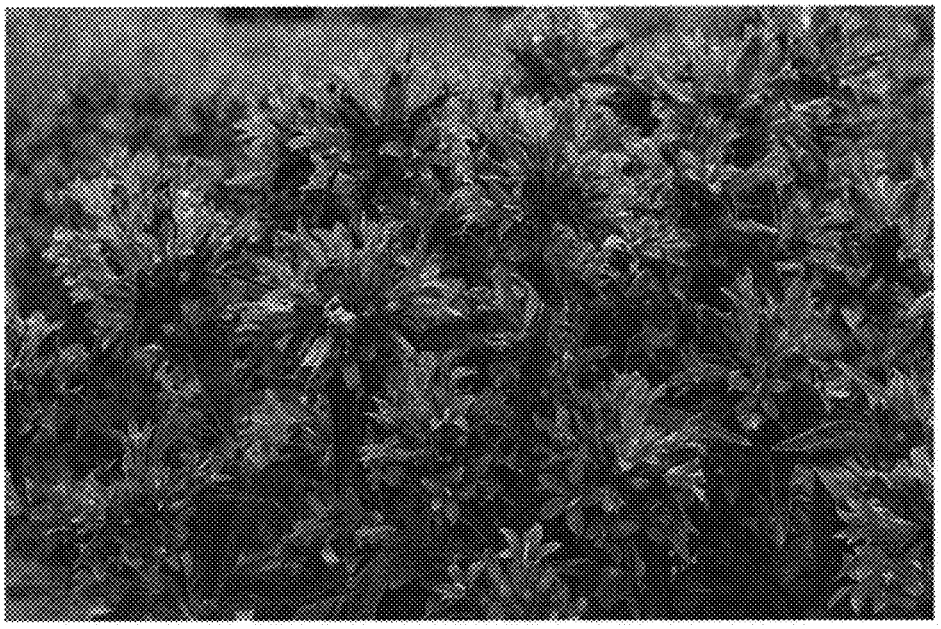
FIG. 2 shows a close-up of the flowers and buds of the new plant.

The following description is based on a four-year-old plant growing in a full-sun trial garden in Zeeland, Mich., USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent "Lavender"; male or pollen parent sibling to "Lavender";

Asexual propagation: Cuttings, about 12 to 20 days to initiate roots; time to finish in a one-gallon container about 9 months;

Plant habit: Up-right, rounded, herbaceous, winter-hardy, perennial mound; with heavily branched flower stems up to 41.0 cm tall and 60.0 cm; average about 40.0 cm tall and about 45.0 cm across;

Leaves: Acaulescent alternate to sub-opposite; cauline opposite and sessile; simple; lanceolate; adaxial and abaxial pubescent; adaxial slightly lustrous; abaxial surface matte; acute apex; attenuate base; margin serrulate and micro-ciliolate; up to 15.5 cm long and 3.8 cm wide, average about 13.0 cm long and 3.0 cm wide;

Leaf color: Young expanding leaves adaxial nearest RHS 138A and abaxial nearest RHS 138A; mature leaves adaxial between RHS 137A and RHS 137B, abaxial between RHS 147C and RHS 147B;

Veins: Reticulate; glabrous adaxial, sparsely puberulent abaxial;

Vein color: Adaxial midrib and main veins nearest RHS 145A and secondary veins nearest RHS 137A, abaxial midrib nearest RHS 145C and secondary veins nearest RHS 147B;

Petiole: On basal leaves only; concavo-convex; clasping base; puberulent adaxial and abaxial; margin ciliolate;

Petiole color: Adaxial and abaxial margin nearest RHS 146B; adaxial center between RHS 146D and RHS 145A; abaxial center nearest RHS 146D;

Flower: Single; perfect; actinomorphic; campanulate; protandrous; on terminal branches; about 40.0 mm long and about 30.0 mm across at apex; attitude outright to slightly upright;

Inflorescence fragrance: Not detected;

Flowering period: Beginning early summer, for about 7 weeks; up to 90 flowers per stem and 65 flowers per average branched stem, and about 2,000 flowers per plant;

Flower longevity: 5 to 7 days;

Flower buds: One day prior to opening—oblong ellipsoidal; rounded apiculate apex and rounded base; about 26.0 mm long and 5.0 mm diameter; heavily fluted longitudinally;

Flower bud color: One day prior to opening—nearest RHS 90D distally and proximally nearest RHS 145D; with petals still folded but separated at apex adaxial nearest RHS N87A and abaxial nearest RHS N87C;

Petals: Typically five in single whorl; lanceolate to linear; acute apex; basal 20.0 mm fused, free and flared in distal 15.0 mm; margin entire; pubescent in basal 23 mm adaxial and glabrous in distal portion, glabrous abaxial; about 35.0 mm long and 6.0 mm wide above fusion;

Petal color (with no change from opening to maturity): Adaxial nearest RHS N87B with distal reticulate veins and petal perimeter between RHS N87A and RHS N87B, adaxial basal 3.0 mm nearest RHS NN155D with mid-portion nearest RHS 85C; abaxial basal 3.0 mm nearest RHS NN155D, proximally above base between RHS N82B and RHS N82C with midrib nearest RHS NN155D in proximal 10.0 mm, middle and distal portion nearest RHS 95C with midrib also nearest RHS 95C; no spots are present either adaxial or abaxial; no change in flower color from opening to maturity;

Corolla: Single; to about 40.0 mm long and 30.0 mm across; fused in basal 20.0 mm; fused portion to about 12.0 mm diameter distally and 4.5 mm diameter at base; lobes slightly reflexed to produce nearly flat face; corolla lobe apices acute;

Androecium: Typically five;

*Filament*.—About 2.0 mm long and flared to 2.0 mm wide at base and constricted to about 0.3 mm diameter in the distal 1.5 mm; color nearest RHS NN155C.

*Anther*.—Very oblong; basifixed; longitudinal; about 9.0 mm long and 1.5 mm across; color nearest RHS 18C.

*Pollen*.—Not abundant; color nearest RHS 11D.

Gynoecium: Single; half-inferior; about 22.0 mm long;

*Style*.—Cylindrical; about 20.0 mm long and 0.5 mm diameter; color between RHS 92D and RHS NN155C.

*Stigma*.—Trifid; decurrent; about 3.0 mm long and 0.5 mm diameter; color nearest RHS NN155B.

*Ovary*.—Ellipsoidal; about 2.0 mm long and 1.5 mm diameter; color between RHS 145A and RHS 145B above petals and RHS 11A beneath petals.

Calyx: Campanulate; to about 21.0 mm long and 20.0 mm wide at apex;

Sepals: Five; linear; narrowly acute apex; fused in the basal 6.0 mm; margin serrulate and ciliolate; glabrous adaxial and abaxial; about 22.0 mm long, about 4.0 mm wide above fusion and 2.0 mm wide at midpoint;

Sepal color: Adaxial nearest RHS 137B distally and nearest RHS 138B proximally, abaxial basal 2.0 mm nearest RHS 145D and distally nearest RHS 137C;

Inflorescence: Panicle with flowers arranged in terminal and axillary clusters; flowering in upper 25.0 cm and 8.5 cm wide;

Peduncle: About 31 per plant; cylindrical, carinate with longitudinal angular ridges along sides of leaf attachment; glabrous; glaucous; upright attitude; strong; heavily-branched; about 8.0 mm diameter at base and 34.0 cm long; about nine nodes, average internode spacing about 3.7 cm; branches to about 12.0 cm long and 4.0 mm diameter at base;

Peduncle color: Nearest RHS 146C;

Pedicel: Cylindrical; glaucous; thin, wiry, strong; average about 2.0 mm long and 0.5 mm diameter;

Pedicel color: Between RHS 145C and RHS 146D;

Seed: Slightly flattened ellipsoidal; rounded apex and base; surface glabrous; about 1.0 mm long and 0.7 mm across center;

Seed color: Variable, some seeds between RHS 165A and RHS 165B;

*Campanula* 'Church Bells' is tolerant of winter temperatures from USDA hardiness at least to zones 4 to 8. The new plant grows best with good drainage and adequate moisture. It is not known to be tolerant of diseases and pest that are common to other *Campanula* cultivars.

I claim:

1. The new and distinct cultivar of *Campanula* plant named 'Church Bells' as described and illustrated.

* * * * *